United States Patent [19]
Allen

[11] Patent Number: 5,498,841
[45] Date of Patent: Mar. 12, 1996

[54] DUAL ACOUSTICAL PASSAGE STETHOSCOPE

[76] Inventor: Derek R. Allen, 1801 Santiago Dr., Newport Beach, Calif. 92660

[21] Appl. No.: 401,956

[22] Filed: Mar. 10, 1995

[51] Int. Cl.⁶ .................................................. H04R 25/00
[52] U.S. Cl. ............................................ 181/137; 181/131
[58] Field of Search ..................................... 181/131, 137

[56] References Cited

U.S. PATENT DOCUMENTS

| | | |
|---|---|---|
| D. 323,033 | 1/1992 | Allen . |
| 3,193,047 | 7/1965 | Allen ........................................ 181/131 |
| 3,570,625 | 3/1971 | Allen . |
| 3,601,218 | 8/1971 | Reynold, Jr. ............................ 181/131 |
| 3,712,409 | 1/1973 | Kizakisz et al. . |
| 4,212,368 | 7/1980 | Allen . |
| 4,569,413 | 2/1986 | Allen . |
| 4,776,426 | 10/1988 | Kazama . |
| 4,823,906 | 4/1989 | Gabriel . |
| 4,928,786 | 5/1990 | Allen . |
| 4,991,686 | 2/1991 | Allen . |

*Primary Examiner*—Khanh Dang
*Attorney, Agent, or Firm*—George F. Bethel; Patience K. Bethel

[57] ABSTRACT

A stethoscope head having a first pair of acoustical passages in sound communication with a low frequency sound receiving bell and a second pair of acoustical passages in sound communication with a high frequency sound receiving diaphragm. A cylindrical valve plug having a third pair of acoustical passages is disposed within a cylindrical bore into which the first and second pairs of acoustical passages open. A pair of sound tubes are connected to the third acoustical passages within the cylindrical valve plug. The pair of sound tubes act as a lever to facilitate rotation of the cylindrical valve plug to acoustically connect the third acoustical passages with either the first or second pair of acoustical passages.

19 Claims, 4 Drawing Sheets

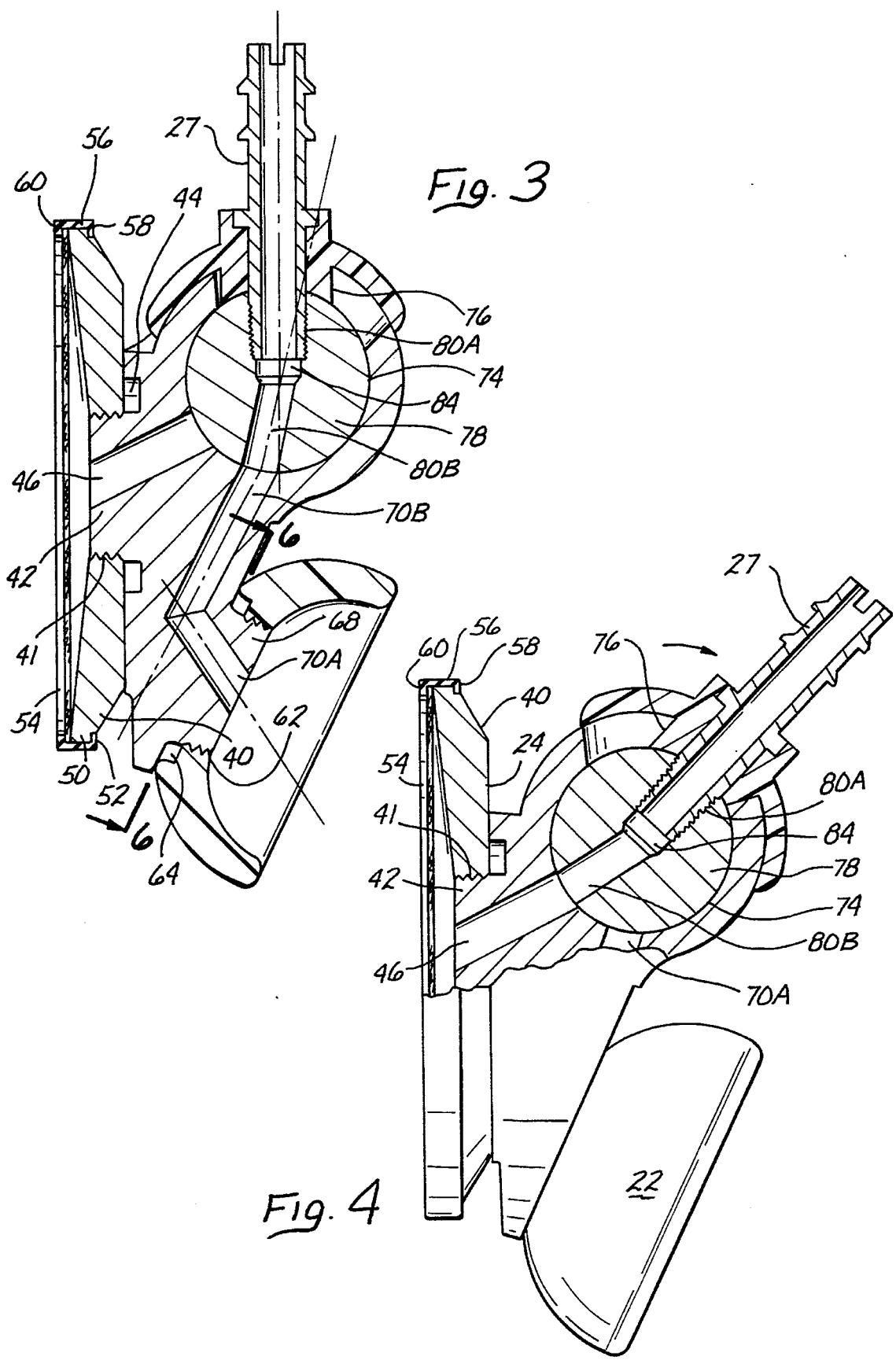

DUAL ACOUSTICAL PASSAGE STETHOSCOPE

FIELD OF THE INVENTION

This invention relates to the field of stethoscopes and particularly to a stethoscope and stethoscope head having two acoustical passages in sound communication with a low frequency sound receiving bell and two acoustical passages in sound communication with a high frequency sound receiving diaphragm. Each member of a pair of acoustical passages forms a continuous acoustical passage through the stethoscope head and valve assembly through one binaural tube to one ear of a user.

DESCRIPTION OF THE PRIOR ART

In my prior patent U.S. Pat. No. 4,212,368 I have disclosed and claimed a dual stethoscope head having a low frequency sound receiving bell which is offset at an acute angle from a high frequency sound receiving diaphragm. A sound tube connected to an airway within a cylindrical valve member acts as a lever to facilitate rotation of the valve member within a cylindrical valve seat or bore within the stethoscope head body. Rotation acoustically connects the bell or the diaphragm to the airway and sound tube which is connected to a flexible sound tube leading to binaurals.

In my U.S. Pat. No. 4,928,786 I disclose and claim a stethoscope head of the type above described which includes a novel cylindrical valve member having a diminished radius half to provide the needed rotational clearance for easy insertion and rotation of the valve in its seat while sealing the sound passages.

In the above described stethoscopes, and with standard conventional stethoscopes, there is a single acoustical passage which is in sound contact with either the bell or with the diaphragm.

In U.S. Pat. No. 4,776,426, there is shown a stethoscope having a bell diametrically opposed to a diaphragm. The bell and the diaphragm are each divided by a partition into two separate semicircular sound receiving chambers. Each semicircular sound receiving chamber communicates with a cylindrical opening for receipt of a tubular shaft. The tubular shaft has a central partition which divides the opening into two acoustical passages which are connected at one end to ear tubes. Rotation of the tubular shaft brings the acoustical passages into communication with the separate openings in either the bell or in the diaphragm.

The disadvantage to the above stethoscope is that in practice, the partition in the bell and in the diaphragm interferes with the acoustic reverberation. The area for sound collection is half as large as for a standard bell or diaphragm.

It is an object of the invention to provide an improved stethoscope and in particular a stethoscope head having two separate acoustical passages opening into a low frequency, sound-receiving bell and two separate passages opening into a high frequency, sound-receiving diaphragm.

It is another object of the invention to provide a stethoscope head having a cylindrical bore with a cylindrical valve member or plug having a pair of acoustical passages which are each at an angle therein.

It is another object of the invention to provide a stethoscope in which one or more pairs of acoustical passages are at an angle within the stethoscope head.

SUMMARY OF THE INVENTION

The stethoscope head of the invention includes a low frequency sound-receiving bell and a high frequency receiving diaphragm. A selectively moveable valve assembly which includes a valve housing having a cylindrical bore valve seat is disposed therein. The first pair of acoustical passages are disposed within the valve-housing and open into an interior surface of the cylindrical bore valve seat or plug for sound communication with the sound receiving bell.

A second set of acoustical passages are disposed within the valve housing and open into the interior surface of the cylindrical bore for sound communication with the high frequency, sound-receiving diaphragm.

A cylindrical valve member or plug is seated within the cylindrical bore valve seat. The cylindrical valve plug has a pair of through channels or airways which are generally disposed radially through the central axis of the cylindrical plug. Each through channel enters the valve plug radially at one angle and exits the valve plug radially at a different angle. A sound tube is disposed within each through channel.

Movement of the sound tube in the manner of a lever permits selective rotation of the valve plug and its acoustical passages for alignment and sound sealing communication with either the first pair of acoustical passages opening into the sound-receiving bell or with the second pair of acoustical passages opening into the high frequency diaphragm.

Each of the two sound tubes is individually connected to one of a pair of binaural tubes. In this manner, there is formed a continuous acoustical passage within each acoustical opening of the sound-receiving bell, through the valve assembly, the sound tubes and flexible tubing, to a right or left ear tip.

Similarly, when rotated into a second position there is formed a continuous acoustical passage within each acoustical opening within the high frequency diaphragm through the valve assembly, the sound tubes and flexible tubing, to a right or left ear tip.

A novel combination locking means in the form of a pair of cylindrical bores or slots are disposed within the valve plug for accommodating a spring and a ball bearing whereby the valve plug is urged into sealing relationship with the aligned acoustical openings. At the same time the cylindrical valve plug is secured against substantial side movement and the rotational position of the valve plug is locked or unlocked with the ball fitting into a groove or detent.

The novel stethoscope of the invention brings the right and left acoustical channel unobstructed through the chest piece into a single cavity chamber of the bell and diaphragm. This effectively produces a greater acoustical response.

The stethoscope of the invention embodying the above features is bilaterally symmetrical.

The invention will be more readily understood by reference to the following drawings taken in connection with the detailed description.

BRIEF DESCRIPTION OF THE DRAWINGS

FIG. 3 is a cross-section showing the acoustical passages of the valve plug in sound receiving alignment with the acoustical passages opening into the sound-receiving bell.

FIG. 4 shows a partial cross-section showing the acoustical passages of the valve plug in sound-receiving alignment with the acoustical passages opening into the high frequency diaphragm;

DETAILED DESCRIPTION OF THE INVENTION

Figure 1:
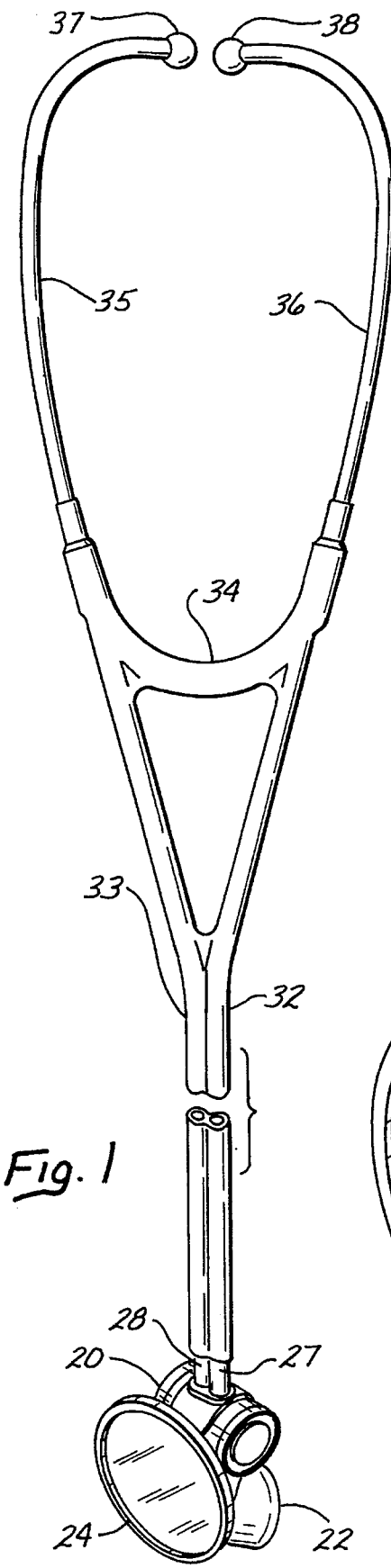
FIG. 1 shows a perspective view of the stethoscope according to the invention.
Figure 1A:
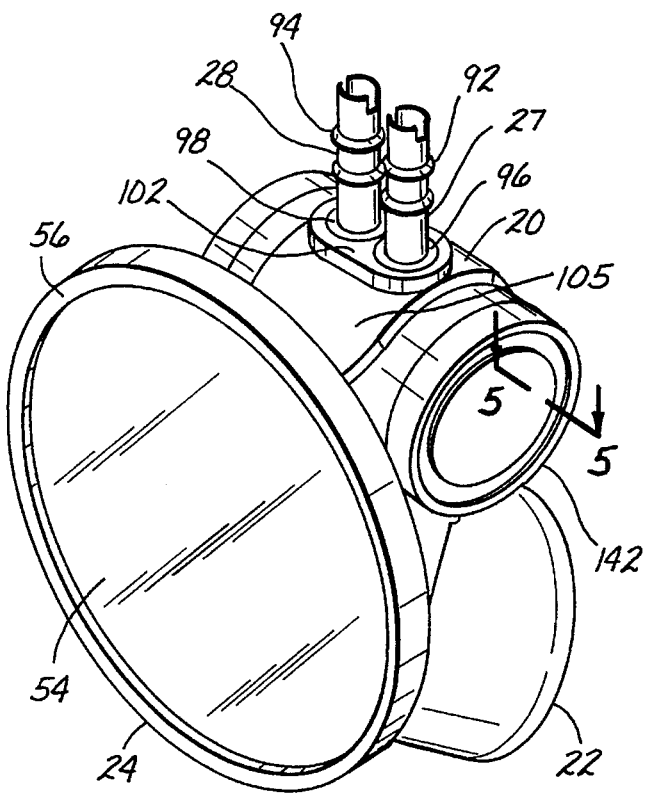
FIG. 1A shows an enlarged perspective view of the stethoscope head of FIG. 1.

As shown in FIGS. 1 and 1A, a stethoscope head 20 includes a stethoscope housing 21 having a low frequency, sound-receiving bell 22 and a diaphragm assembly 24. A pair of airway or sound tubes 27 and 28 are connected to flexible tube binaurals 32 and 33 which are united by a yoke 34 having a spring member not shown and which is connected to metal sound tubes 35 and 36 which are capped with ear tips 37 and 38.

Figure 2:
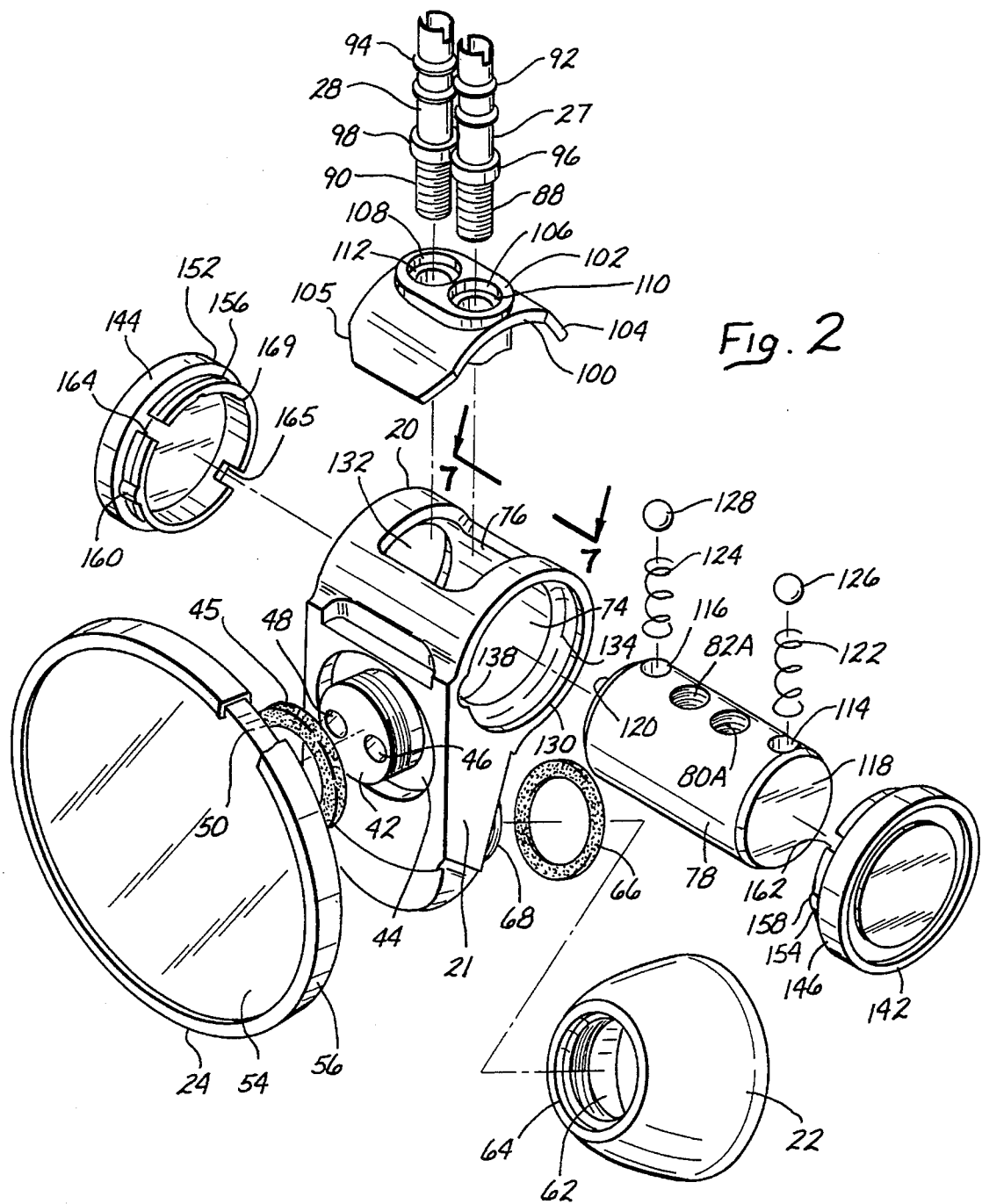
FIG. 2 shows an exploded view of the stethoscope head with the various parts removed to show the assembly.

The separated parts of the stethoscope head 20 can be seen in the exploded view of FIG. 2, and FIGS. 3, and 4. In viewing FIGS. 3 and 4, it should be noted that the stethoscope head is bilaterally symmetrical and only half of the pairs of acoustical passages are shown.

The diaphragm assembly 24 includes a plate 40 having an interiorly threaded opening 41 which is connected to an exteriorly threaded, upstanding, cylindrical member 42 on stethoscope housing 21. A circular channel 44 surrounds the cylindrical member 42 for accommodating an O-ring 45 for sound sealing. A pair of acoustical passages 46 and 48 are disposed at an angle within the cylindrical member 42 for communication with a valve assembly.

The diaphragm plate 40 is provided with a shoulder 52 and a flange 50 which surrounds the diaphragm plate 40. The diaphragm 54 in the form of a plastic disk is held against the bottom of the diaphragm plate 40 by means of a flexible ring gasket 56.

The gasket 56 includes an interior peripheral channel and two upstanding peripheral flanges 58 and 60. One peripheral flange 58 seats on the shoulder 52 of the diaphragm plate 40 while other flange 60 encloses the diaphragm flange 50 of the diaphragm plate 40 and the peripheral edge of diaphragm 54.

As shown in the exploded view of FIG. 2, and FIGS. 3, 4, 6 and 7, the sound receiving bell 22 includes a bell in the form of a generally concave cross-sectional configuration forming a bowl-like member. The bell 22 has a central aperture 62 which is interiorly threaded.

On the underside of the exterior of the bell surrounding the central aperture is a recessed circular channel 64 for seating of an O-ring 66. The threaded central aperture 62 receives an upright cylindrical member 68 having two acoustical passages 70A and 72A therein for communication with a valve assembly.

The valve assembly is detailed in FIGS. 2–4 and 7. The stethoscope housing 21 has a substantially cylindrical central bore 74 which acts as a valve seat. A side wall opening 76 communicates with the cylindrical valve seat 74 for accommodation and movement of the airway or sound tubes 27 and 28.

Figure 7:
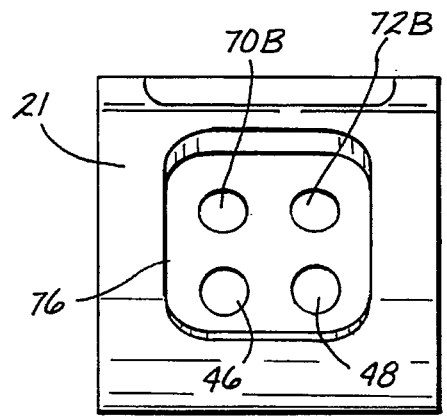
FIG. 7 shows a view of the acoustical passages of the cylindrical valve seat or bore from the direction of 7—7 of FIG. 2.

Within the valve housing 21 and opening into the cylindrical valve seat 74 as seen particularly in FIG. 7, there are provided a first pair of acoustical passages 70B and 72B which communicate with the bell 22 through upright cylindrical member 68 and a second pair of acoustical passages 46 and 48 which communicate acoustically through the upright cylindrical member 42 with the diaphragm plate 40 and the diaphragm 54.

The acoustical passages 70A and 70B, and 72A and 72B which communicate with the bell 22 are each formed of two intersecting passages or conduits. As shown in FIG. 3, passages 70A and 70B, each have a central axis which intersects the other axis at an included angle of about 60° to about 70°. Similarly, passages 72A and 72B, which are hidden in the showing of FIG. 3, each have a central axis which intersects the other axis at an included angle of about 60° to about 70°. However, other angles can be utilized to bring the passages 70B and 72B into unobstructed alignment with the acoustical passages 80B and 82B within the valve plug 78.

As shown in FIGS. 3 and 4, the acoustical passage 46 and acoustical passage 48 which is hidden in FIGS. 3 and 4, which communicate with the diaphragm 24 through upright cylindrical member 42 each have a central axis which is straight.

A cylindrical body member or valve plug 78 is seated within the valve seat 74. A third pair of acoustical passages 80A, 80B shown in FIG. 3 and 82A, 82B hidden in FIG. 3 are disposed within the cylindrical valve plug or body member 78 for selective communication upon rotation with either the first pair of acoustical passages 46 and 48 or with the second pair of acoustical passages 70A, 70B and 72A, 72B.

In this manner, alignment of the first pair of acoustical passages 46 and 48 or the second pair of acoustical passages 70A, 70B and 72A, 72B with the third acoustical passages 80A, 80B and 82A, 82B forms a pair of a continuous uninterrupted acoustical or sound pathways.

Each member of the third pair of acoustical passages 80A, 80B and 82A, 82B is formed of two intersecting openings or channels. Each opening or channel has a central axis which intersects the axis of the continuing opening or channel at an included angle of about 18°. However, other angles can be utilized to bring the passages 80B and 82B into alignment upon rotation of the valve plug 78 with the acoustical passages 70B and 72B and into alignment with acoustical passages 46 and 48 opening into the valve seat 74.

Each member of each third pair acoustical passages formed of openings or channels 80A, 80B and 82A, 82B is also disposed radially within the side wall of valve plug 78 to perpendicularly intersect the central axis of the valve plug 78.

As shown in FIG. 2, openings 80A and 82A of the third acoustical passages contain interior threads and a shoulder or seat 84 shown in FIG. 3 and 86 hidden in FIG. 3 respectively for receiving an exteriorly threaded end 88 and 90 respectively of airway sound tubes 27 and 28.

The sound tubes 27 and 28 have a plurality of exterior ridges or flanges 92 and 94 and a stop in the form of shoulders 96 and 98 respectively. A flexible binaural sound tube 32 and 33 can be slip fit over the ridges or flanges 92 and 94 respectively as shown in FIGS. 1 and 2.

A saddle member 100 has a substantially central body member 102 extending above and below adjacent wings 104 and 105. A pair of openings 106 and 108 having a recessed inner flange 110 and 112 respectively are disposed within the saddle body member 102. The sound tubes 27 and 28 are inserted within the openings 106 and 108 in the body member 102 and threaded until the shoulders 96 and 98 are seated within the inner flange 110 and 112 respectively.

The body member 102 fits within the opening 76 in the valve seat 74 while the wings 104 and 105 are curved to follow the exterior curve of the stethoscope body 21.

Figure 3A:
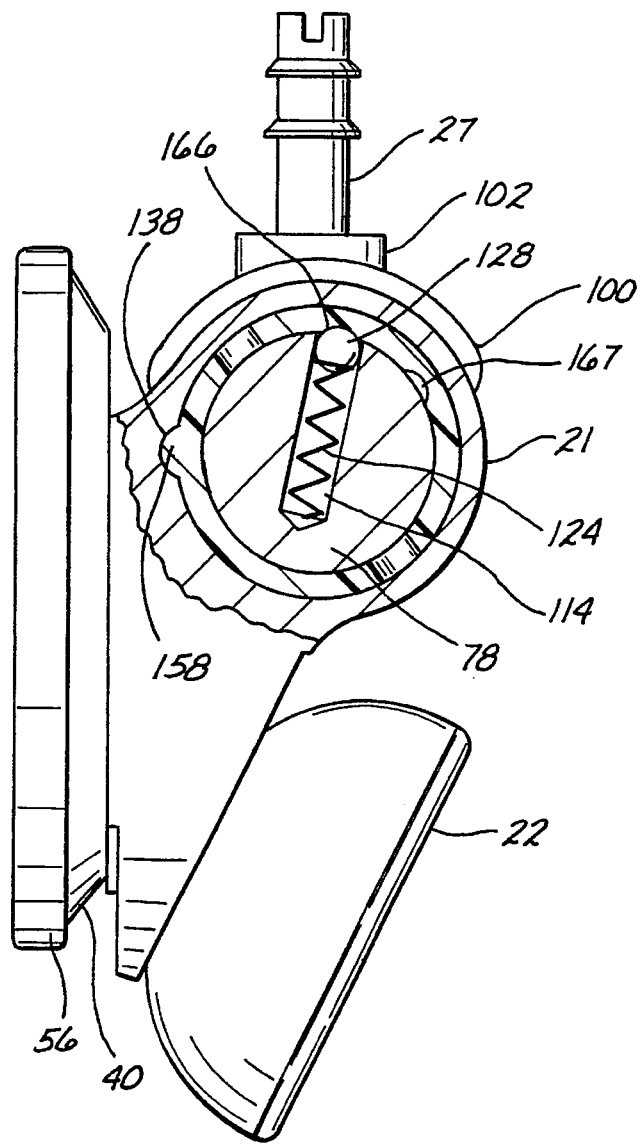
FIG. 3A shows a partial section detailing the mechanism for sound-sealing the valve member or plug within the cylindrical bore valve seat and the means for securing the valve in one or another position.

As shown in FIGS. 2 and 3A, the valve plug member 78 also includes a pair of radial slots or bores 114 and 116, hidden in FIG. 3A, adjacent the ends 118 and 120, hidden in FIG. 3A, of the cylindrical valve plug 78. The central axis of slots or bores 114 and 116 passes radially in a perpendicular direction through the central axis of the valve cylinder plug 78. The central axis of the slots 144 and 116 are parallel to the central axis of passages 80B and 82B. This provides a radial thrust as seen hereafter to acoustically seal the passages 80B and 82B.

The primary function of the slots 114 and 116 is to urge the valve plug 78 against the opposite side of the valve seat 74. This is effectively achieved by making the central axes parallel as above described. This provides sound sealing when the third acoustical passages 80B and 82B are in sound communication with either the first acoustical passages 46 and 48 or the second acoustical passages 70B and 72B within the stethoscope body 21.

The slots or bores 114 and 116 do not pass completely through the valve cylinder member 78. Each slot 114 and 116 accommodates a spring 122 and 124 and a ball 126 and 128 respectively. As shown particularly in FIGS. 2 and 3A, each end 130 and 132 of the cylindrical valve seat 74 includes a recessed shoulder or interior ridge 134 and 136 respectively.

Each recessed shoulder 134 and 136 within the valve seat 74 acts as a stop for the balls 126 and 128 within the cylindrical valve member 78 to prevent side movement and removable of the valve plug 78 from the valve seat 74.

In addition, in each wall area between the shoulders 134 and 136 and the ends 130 and 132 of the valve seat 74 is a small interior groove or channel 138 and 140 (not shown) respectively.

As shown in FIG. 2, the valve plug member 78 with the slots 114 and 116 filled with the springs 122 and 124 and balls 126 and 128 respectively is inserted within the valve seat 74 with the slots closest to the bell 22. The saddle body member 102 fits within the opening 76 within the valve seat 74 and a pair of sound tubes 27 and 28 are inserted through the openings 106 and 108 within the saddle body 102 and threaded into the third acoustical passages or channels 80A and 82B within the valve plug member 78.

Figure 5:
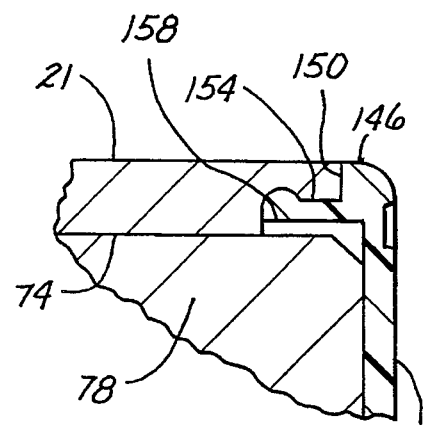
FIG. 5 shows a cross-section taken along the lines 5—5 of FIG. 1A.
Figure 6:
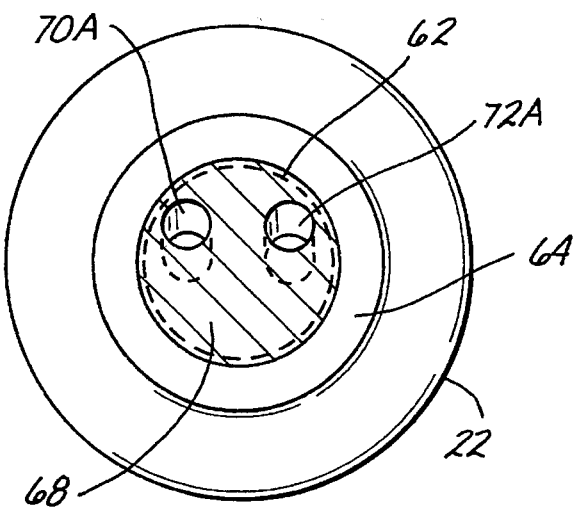
FIG. 6 shows a section taken along the lines 6—6 of FIG. 3 and shows the acoustical openings within the low frequency, sound-receiving bell.

A right and left end cap 142 and 144 fit over each end 118 and 120 respectively of the valve plug member 78 to cover the slots 114 and 116 and balls 126 and 128 at each end. As shown in FIGS. 2, 3A, and 5, each end cap 142 and 144 is formed of an outer flange 146 and 148 having a flat ridge or shoulder 150 and 152 respectively adjacent an inner flange 154 and 156 of smaller diameter.

The inner flanges 154 and 156 are provided with an exterior protuberance or bump 158 and 160 and a pair of through slots 162 and 163, and 164 and 165 respectively. The interior of each cap 142 and 144 is provided with two lengthwise semicircular open channels or grooves 166 and 167, and 168 (not shown) and 169 respectively.

The end caps 142 and 144 are frictionally fit within the end portion 118 and 120 of the valve plug 78 over the balls 126 and 128. Placement of the end caps 142 and 144 is facilitated by the slots 162 and 163, and 164 and 165 respectively.

The exterior protuberance or bump 158 and 160 of the end caps 142 and 144 respectively fits within the inner groove or channel 138 and 140 at the end portion 130 and 132 of the valve seat 74. This acts to keep the end caps 142 and 144 in a stationary or fixed position.

The pair of slots 162 and 163, and 164 and 165 function to allow compression of the inner flange 154 and 156 respectively for insertion and tight fit. The inner open grooves or channels 166 and 167, and 168 and 169 within the end caps 142 and 144 function as limit stops or detents for the balls 126 and 128. In this manner, rotation of the cylindrical valve plug 78 will stop exactly at the point of alignment of the third acoustical passages 84A, 84B, and 86A, 86B with either the first acoustical passages 46 and 48 or with the second acoustical passages 80A, 80B, and 82A, 82B.

The stethoscope head of the invention can be formed of metal, plastic or other materials or combinations. In the preferred embodiment, the valve housing, valve plug, and diaphragm plate are formed of a metal while the bell is formed of a rigid plastic.

The stethoscope of the invention provides particular advantages of a large area sound receiving bell and diaphragm with sound sealed acoustical transmission to each ear of a user from the bell and from the diaphragm.

Switching from the bell to the diaphragm is easily and conveniently achieved using one hand. Moreover, the switching means effectively combines sound sealing acoustical passages, securing in a first or a second position, and securement against lateral movement.

Various modifications of the invention are contemplated and can be resorted to without departing from the spirit and scope of the invention as defined by the following attached claims.

I claim:

1. A stethoscope head comprising:

a low frequency sound receiving bell;

a high frequency sound receiving diaphragm;

a selectively movable valve assembly comprising a valve housing having a cylindrical bore valve seat having an axis and an interior surface;

said bell and said diaphragm being offset at an angle from each other;

a substantially cylindrical valve plug having an axis, two ends, and an exterior surface, said valve being seated within said cylindrical bore valve seat;

a first pair of acoustical passages within said valve housing which open into said interior surface of said cylindrical bore for sound communication with said bell;

a second pair of acoustical passages within said valve housing which open into said interior surface of said cylindrical bore for sound communication with said diaphragm;

a third pair of acoustical passages within said valve plug for selective alignment and sound communication with said first pair of acoustical passages and with said second pair of acoustical passages upon rotation of said cylindrical valve plug within said cylindrical bore;

a pair of sound tubes connected to said third pair of acoustical passages whereby one acoustical passage of said first pair of acoustical passages or one acoustical passage of said second pair of acoustical passages, one acoustical passage of said third pair of acoustical passages, and one of said sound tubes forms a continuous sound passageway for conducting sound from said bell or from said diaphragm, through said housing, through said valve plug, and through said sound tube to one ear of a user; and, wherein the other one of said first pair of acoustical passages or the other one of said second pair of acoustical passages, the other one of said third pair of acoustical passages, and the other one of said sound tubes forms a continuous sound passageway for conducting sound from said bell or from said diaphragm, through said housing, though said valve plug, through said sound tube to the other ear of a user.

2. A stethoscope head according to claim 1 further comprising:

means within said valve seat and said valve plug for urging said third pair of acoustical passages into sound sealing contact with said first pair or with said second pair of acoustical passages upon rotation of said cylindrical valve plug.

3. A stethoscope head according to claim 1 further comprising:

means connected to said cylindrical valve plug for selectively moving said cylindrical valve plug for alignment of said third pair of acoustical passages with said first pair or with said second pair of acoustical passages.

4. A stethoscope head as claimed in claim 3 wherein said cylindrical valve plug has an axial center and further comprises:

at least one side wall slot which passes radially in a perpendicular direction through the axial center of the cylindrical valve plug; and, a spring and a ball disposed within each said slot for urging said cylindrical valve plug and said third acoustical passages into sound sealing contact with said first pair or with said second pair of acoustical passages within said cylindrical bore valve seat upon rotation of said valve plug.

5. A stethoscope head as claimed in claim 4 wherein said cylindrical bore forming said valve seat further comprises:

a side wall opening within said cylindrical bore for accommodation of said pair of sound tubes connected to said third pair of acoustical passages of said cylindrical valve plug and sized to permit selective rotation of said valve plug and said sound tubes to align said third acoustical passages with said first pair or with said second pair of acoustical passages.

6. A stethoscope head as claimed in claim 5 wherein:

said sound tubes act as a lever and each sound tube comprises a section of a hollow tube having means at one end for attachment to one of said cylindrical valve plug third acoustical passages and means at the other end for attachment to a flexible sound tube.

7. A stethoscope head as claimed in claim 6 wherein said cylindrical bore has an axial center and said locking means comprises:

a pair of end channels in said cylindrical bore valve seat;

said slots of said cylindrical valve plug being disposed adjacent the ends of said valve plug; and, a ball disposed within each said slot of said cylindrical valve plug between said spring and one of said end channels of said cylindrical bore so that said spring locks said ball within one of said end channels thereby substantially locking said valve against lengthwise movement.

8. A stethoscope according to claim 7 further comprising:

end caps for said valve plug ends which are received within said end channels of said cylindrical valve bore;

means for locking said end caps against rotation;

first and second detent means for said balls so that said valve plug is stopped against rotation within said cylindrical valve seat when said third acoustical passages of said valve plug are aligned with said first acoustical passages and is stopped against rotation when said third acoustical passages of said valve plug are aligned with said second acoustical passages upon rotation of said valve plug between said first and said second detent means.

9. An acoustically self-sealing stethoscope head comprising:

a housing;

a cylindrical bore disposed within said housing;

a cylindrical valve plug seated and supported within said cylindrical bore to form a selectively movable valve assembly;

a first body portion within said housing having a pair of first acoustical passages disposed therein which are in sound communication with said cylindrical bore;

a low frequency sound receiving bell in sound communication with said first acoustical passages;

means for attachment of said bell to said first body portion;

a second body portion within said housing having a second pair of acoustical passages therein which are in sound communication with said cylindrical bore;

a diaphragm plate and a diaphragm, said diaphragm plate having means for attachment to said second body portion so that said diaphragm is in sound communication with said second pair of acoustical passages;

means for attachment of said diaphragm to said diaphragm plate;

said first body portion and said second body portion being offset at an angle to one another;

said cylindrical valve plug having a third pair of acoustical passages for communication with said first acoustical passages within said first body portion for sound communication with said bell when said valve plug is rotated to a first position, and for sound communication with said second acoustical passages within said second body portion for sound communication with said diaphragm when said valve plug is rotated to a second position;

at least a portion of each one of said third pair of acoustical passages including a radial bore for selective alignment with said first and said second acoustical passages within said cylindrical bore upon rotation of said valve plug; and, means connected to said cylindrical valve plug for selectively moving said valve plug between said first and said second acoustical passages.

10. A stethoscope as claimed in claim 9 wherein:

said bell and said first body portion are cooperatively threaded for removably attaching said bell to said first body portion.

11. A stethoscope as claimed in claim 8 wherein said diaphragm plate and said second body portion are cooperatively threaded for removably attaching said diaphragm plate to said second body portion.

12. A stethoscope as claimed in claim 10 further comprising:

means within said valve assembly disposed within said cylindrical valve plug for urging said third pair of acoustical passages within said cylindrical valve plug into sound sealing contact with said first pair or said second pair of acoustical passages within said cylindrical bore upon rotation of said valve plug.

13. A stethoscope as claimed in claim 11 wherein:

each of said third acoustical passages of said cylindrical valve plug includes at least one radial portion which is in direct alignment with said first or said second acoustical passages, each of said radial passages having a central axis;

at least one radial slot disposed within said cylindrical valve plug, each slot having an axis which is parallel to the axis of said radial portion of said third acoustical passage; and, a spring and a ball disposed within said at least one radial slot of said valve plug for urging said third acoustical passages of said cylindrical valve plug into sound sealing contact with said first pair or with said second pair of acoustical passages.

14. A stethoscope as claimed in claim 13 further comprising:

an opening within said housing in communication with said cylindrical bore valve seat for access to said third acoustical passages;

a hollow tubular member attached through said opening to each one of said pair of third passages within said cylindrical valve plug to provide sound communication therewith; and, detent means within said cylindrical bore valve seat for selectively locking with said ball into sound sealing communication with said first or said second pair of acoustical passages upon movement of said hollow tubular members.

15. A stethoscope head according to claim 14 further comprising:

said third acoustical passages each being formed of a fourth radial passage and a fifth radial passage, each having a central axis which intersects the other;

said fifth radial passages opening into contiguous contact with said first pair or with said second pair of acoustical passages; and, said central axes of said fifth radial passages being parallel to said central axes of said radial slots within said cylindrical valve plug.

16. A stethoscope head according to claim 15 wherein:

said first acoustical passages are formed of a sixth acoustical passage and a seventh acoustical passage, each having a central axis which intersects the other.

17. The combination of the stethoscope head of claim 1 and binaural tubes.

18. A stethoscope head according to claim 9 which is bilaterally symmetrical.

19. A stethoscope head comprising:

a low frequency sound receiving bell a high frequency sound receiving diaphragm and a diaphragm plate;

a valve housing;

a cylindrical bore valve seat disposed within said valve housing:

a cylindrical valve plug having ends and disposed within said valve seat;

a first pair of acoustical passages disposed within said valve housing which are in sound communication with said bell and with said valve seat, each member of said first pair of acoustical passages being formed of two intersecting conduits;

a second pair of acoustical passages disposed within said valve housing which are in sound communication with said diaphragm and with said valve seat;

a third pair of acoustical passages disposed within said cylindrical valve plug which are selectively aligned for sound communication with said first acoustical passages and with said second acoustical passages within said valve seat, each member of said third pair of acoustical passages being formed of two intersecting conduits each disposed radially of said valve plug, one of said intersecting radially conduits having an opening for alignment with said first or said second acoustical passages opening into said valve seat;

a pair of radial slots disposed adjacent the ends of said cylindrical valve plug, said slots being parallel to said intersecting conduits of said valve plug which have an opening for alignment with said first or said second acoustical passages; and, a spring and a ball disposed within said slots for providing a radial thrust against said valve seat to seal said third acoustical passages against said first or said second pair of acoustical passages opening into said valve seat.

\* \* \* \* \*